United States Patent
Molho et al.

(10) Patent No.: US 8,834,807 B2
(45) Date of Patent: *Sep. 16, 2014

(54) DEVICE AND METHOD FOR IMPROVING SAMPLE INJECTION AND STACKING

(75) Inventors: Josh Molho, Los Altos, CA (US); Hui Xu, Palo Alto, CA (US)

(73) Assignee: Caliper Life Sciences, Inc., Hopkinton, MA (US)

( * ) Notice: Subject to any disclaimer, the term of this patent is extended or adjusted under 35 U.S.C. 154(b) by 223 days.

This patent is subject to a terminal disclaimer.

(21) Appl. No.: 13/287,071

(22) Filed: Nov. 1, 2011

(65) Prior Publication Data
US 2012/0043206 A1 Feb. 23, 2012

Related U.S. Application Data

(63) Continuation-in-part of application No. 12/843,557, filed on Jul. 26, 2010, now Pat. No. 8,202,486.

(60) Provisional application No. 61/409,772, filed on Nov. 3, 2010, provisional application No. 61/233,392, filed on Aug. 12, 2009, provisional application No. 61/266,030, filed on Dec. 2, 2009.

(51) Int. Cl.
| | |
|---|---|
| *B01D 17/06* | (2006.01) |
| *C12M 1/34* | (2006.01) |
| *C12M 1/36* | (2006.01) |
| *G01N 21/05* | (2006.01) |
| *B01L 3/00* | (2006.01) |
| *G01N 27/447* | (2006.01) |

(52) U.S. Cl.
CPC .... *G01N 27/44791* (2013.01); *G01N 27/44717* (2013.01); *B01L 2400/0655* (2013.01); *B01L 2300/0816* (2013.01); *B01L 3/502753* (2013.01); *B01L 2400/0421* (2013.01); *B01L 2200/0636* (2013.01); *B01L 3/502738* (2013.01)
USPC .............. 422/255; 422/50; 422/68.1; 422/82; 422/549; 204/450; 204/600; 137/13; 137/861; 435/286.2; 435/287.1; 435/288.6; 435/288.7

(58) Field of Classification Search
None
See application file for complete search history.

(56) References Cited

U.S. PATENT DOCUMENTS

| | | |
|---|---|---|
| 4,608,147 A | 8/1986 | Clad |
| 5,140,161 A | 8/1992 | Hillman et al. |

(Continued)

FOREIGN PATENT DOCUMENTS

| | | |
|---|---|---|
| WO | 0151918 A1 | 7/2001 |
| WO | 03013703 A1 | 2/2003 |
| WO | 2010042766 A1 | 4/2010 |

OTHER PUBLICATIONS

A.E. Kelly et al., Low-conductivity buffers for high-sensitivity NMR measurements, 2002, J. Am. Chem. Soc., 124: 12013-12019.*

(Continued)

*Primary Examiner* — Jill Warden
*Assistant Examiner* — Timothy G Kingan
(74) *Attorney, Agent, or Firm* — Cardinal Law Group (57) ABSTRACT

The invention provides devices and methods for isolating one or more sample components of a sample material following separation of the sample material into a plurality of sample components. A device includes a separation channel having a sample loading well. A low-conductivity buffer is disposed in the loading well, the buffer having a conductivity<0.2 mS/cm. In a method, a buffer is loaded into a loading well in fluid communication with a separation channel of a device. A sample material having a conductivity higher than that of the buffer is then loaded into the loading well such that the sample material is disposed beneath the buffer, the buffer disposed over and covering the sample material. The sample material is separated into a plurality of separated components in the separation channel, and a separated component is collected from a collection well disposed in a collection leg of the device.

24 Claims, 8 Drawing Sheets

(56) References Cited

U.S. PATENT DOCUMENTS

| | | | |
|---|---|---|---|
| 5,827,418 | A | 10/1998 | Haven et al. |
| 6,270,641 | B1 | 8/2001 | Griffiths et al. |
| 6,485,625 | B1 | 11/2002 | Simpson et al. |
| 6,506,609 | B1 | 1/2003 | Wada et al. |
| 7,419,784 | B2 | 9/2008 | Dubrow et al. |
| 8,062,903 | B2 * | 11/2011 | Chiu et al. .................... 436/174 |
| 2002/0127736 | A1 | 9/2002 | Chou et al. |
| 2003/0017493 | A1 * | 1/2003 | Fremont et al. .................... 435/6 |
| 2003/0044832 | A1 | 3/2003 | Blankenstein |
| 2003/0075446 | A1 * | 4/2003 | Culbertson et al. ........... 204/451 |
| 2005/0205427 | A1 | 9/2005 | Boschetti et al. |
| 2007/0287683 | A1 * | 12/2007 | Shriver et al. .................... 514/56 |
| 2008/0261295 | A1 * | 10/2008 | Butler et al. ............... 435/286.5 |
| 2010/0126862 | A1 | 5/2010 | Sabin et al. |

OTHER PUBLICATIONS

D. Huh, et al Gravity-driven microfluidic particle sorting device with hydrodynamic separation amplification, 2007, Anal. Chem. 79: 1369-1376.*

D. Huh, et al Gravity-driven microfluidic particle sorting device with hydrodynamic separation amplification, 2007, Analytical Chemistry, 79: 1369-1376.*

H. Tsutsui and C-M. Ho, Cell separation by non-inertial force fields in microfluidic systems, 2009, Mechanics Research Communications, 36: 92-103.*

Effenhauser et al., "Manipulation of sample fractions on a capillary electrophoresis chip." Analytical Chemistry, vol. 67, No. 13, pp. 2284-2287, Jul. 1, 1995; American Chemical Society, US.

Griffiths et al., "Low-dispersion turns and junctions for microchannel systems." Analytical Chemistry, vol. 73, No. 2, pp. 272-278, Jan. 15, 2001; American Chemical Society, US.

Jacobson et al., "Electrokinetic focusing in microfabricated channel structures." Analytical Chemistry, vol. 69, No. 16, pp. 3212-3217, Aug. 15, 1997; American Chemical Society, US.

Li et al., "Design, simulation, and optimization of a miniaturized device for size-fractioned DNA extraction." Electrophoresis, vol. 28, pp. 4661-4667, 2007; Wiley-VCH Verlag Gmbh & Co. KGaA, Weinheim.

Lin et al., "Selective extraction of size-fractionated DNA samples in microfabricated electrophoresis devices." Journal of Chromatography A, vol. 1010, pp. 255-268, 2003; Elsevier BV, Netherlands.

Zalewski et al., "Electrophoretic sorting and collection of fractions for preparative capillary electrophoresis on a chip." Lab on a Chip, vol. 8, No. 5, pp. 801-809, 2008; Royal Society of Chemistry, UK.

* cited by examiner

DEVICE AND METHOD FOR IMPROVING SAMPLE INJECTION AND STACKING

TECHNICAL FIELD

The present disclosure is in the field of devices and systems for separation and isolation of sample components and methods for their use. In particular, described herein are devices and methods for isolating one or more sample components of a sample material following separation of the sample material into a plurality of sample components.

This application is a continuation-in-part of Ser. No. 12/843,557 filed Jul. 26, 2010, and claims the benefit of U.S. Provisional Application No. 61/233,392 filed Aug. 12, 2009, U.S. Provisional Application No. 61/266,030 filed Dec. 2, 2009, and U.S. Provisional Application No. 61/409,772 filed Nov. 3, 2010, the disclosures of which are herein incorporated by reference.

BACKGROUND OF THE INVENTION

Separations-based analyses are a prominent part of biological research, allowing one to characterize different biological samples, reaction products and the like. Examples of some of the more prevalent separations-based analyses include electrophoretic separations of macromolecular species, e.g., proteins and nucleic acids. Electrophoresis, e.g., capillary electrophoresis, has been established as a highly effective method for separating macromolecular species in order that they might be further characterized. Protein and nucleic acid molecules are two major examples of molecular species that are routinely fractionated and characterized using electrophoretic systems.

Both microfluidic and macrofluidic devices have been applied in separations-based analyses. Examples of novel microfluidic devices and methods for use in the separation of molecular, and particularly macromolecular species by electrophoretic means are described in U.S. Pat. Nos. 5,958,694, 6,032,710, and 7,419,784, for example, the entire contents of which are incorporated by reference herein. In such devices, the sample containing the macromolecular species for which separation is desired is placed in one end of a separation channel located in a microfluidic substrate and a voltage gradient is applied along the length of the channel. As the sample components (also referred to as "fragments") are electrophoretically transported along the length of the channel and through the separation (sieving) matrix disposed therein, those components are resolved. The separated components are then detected at a detection point along the length of the channel, typically near the terminus of the separation channel downstream from the point at which the sample was introduced. Following detection, the separated components are typically directed to a collection reservoir/well in the device (or to an external device such as a multiwell plate via a capillary pipettor, for example) for subsequent extraction or disposal.

In many situations, it is desirable to extract selected fragments of interest, such as DNA (deoxyribonucleic acid) fragments, following the separation of the fragments into bands in the separation matrix for further processing or analysis, e.g., restriction enzyme modification, T4 ligation, PCR (polymerase chain reaction) amplification, mass spectroscopy, or polynucleotide kinase reactions. The typical process used by laboratory researchers for extracting and isolating selected DNA fragments of interest (and other desired nucleic acid and protein fragments) from a separation matrix (such as an agarose gel) involves staining the separated fragments and then shining ultraviolet (UV) light on the fragments to visualize the separated bands. A razor blade is then used to manually cut the gel above and below each fragment of interest. The DNA must then be extracted and purified from the gel slice. The recovered DNA can then be used for further processing or analysis. This extraction process, however, is time consuming, laborious, and potentially damaging to the DNA (e.g., nicking of the DNA can occur if the DNA is exposed to UV light too long while the fragments of interest are being illuminated for excision).

Thus, in performing separations-based analyses, it would be desirable to be able to also isolate or extract one or more of the separated components in the device itself for further analysis or processing. The recovered or isolated fragments could then be used for a variety of different processes including, for example, the following: amplification using polymerase chain reaction (PCR); ligation reactions for cloning small to medium-sized strands of DNA into bacterial plasmids, bacteriophages, and small animal viruses to allow the production of pure DNA in sufficient quantities to allow its chemical analysis; adapter ligation used in high-throughput sequencing; reactions to dissolve a separated protein or nucleic acid component in a suitable matrix for further analysis by a mass spectrometer using, for example, Matrix-Assisted Laser Desorption Ionization (MALDI); binding reactions to bind a labeling agent to one or more separated protein or nucleic acid components for further analysis; or other similar post-detection processes. In addition, in the case of PCR samples, it is important to be able to separate smaller dimer and primer molecules from the main nucleic acid fragments in the sample and then isolate and collect the main nucleic acid fragments for further analysis or processing, while directing the smaller primer and dimer components to a waste reservoir/cell for removal and subsequent disposal.

A standard reference of known size is obtained by separating a standard DNA sizing ladder, e.g., for DNA separations, or a standard polypeptide of known molecular weight, e.g., for protein separations. Such a sizing ladder allows the size of unknown fragments to be determined. In a typical separation assay without fractionation (i.e., without isolation of components), the step of separating a standard sizing ladder is performed prior to transporting the first sample material through the separation channel to separate the sample material into a plurality of sample components. Thus, the entire ladder and all separated sample components have passed the detector before any sizing analysis is performed. Alternatively, a ladder may be run in parallel with a sample. In either case, the entire ladder and all separated sample components have passed a detector before any sizing analysis is performed.

To permit fractionation, a sizing analysis must be performed prior to the sample component(s) of interest passing the detector, thereby allowing a selected one or more separated components of interest to be diverted from the separation channel to a sample component collection location based on the determined size of the selected one or more sample components.

Thus, it would be advantageous to provide devices and methods that include a low-conductivity buffer in a sample loading well to improve sample injection and stacking when separating a sample material into a plurality of sample components.

SUMMARY OF THE INVENTION

One aspect of the present invention is a device for isolating one or more sample components of a sample material following separation of the sample material into a plurality of sample components. The device comprises a separation channel having first and second ends. A loading well is disposed in the separation channel, and a quantity of a buffer is disposed in the loading well. The buffer has a conductivity<0.2 mS/cm. The device includes a collection leg having first and second ends, the collection leg having a collection well disposed between the first and second ends, a waste leg having first and second ends, and a switching region having an inlet end and an outlet end. The second end of the separation channel is in fluid communication with the inlet end of the switching region, and the first end of the collection leg and the first end of the waste leg are in fluid communication with the outlet end of the switching region.

Another aspect of the present invention is a method for isolating one or more sample components of a sample material following separation of the sample material into a plurality of sample components. The method comprises loading a buffer into a loading well in fluid communication with a separation channel of a device, the buffer having a first conductivity; loading a sample material into a loading well such that the sample material is disposed beneath the buffer, the buffer disposed over and covering the sample material, the sample material having a second conductivity, the second conductivity being higher than the first conductivity; separating the sample material into a plurality of separated components in the separation channel, the separated components forming a stream; transporting the stream of separated components into a switching region of the device; directing a first portion of the stream of separated components out of the switching region and into a waste leg of the device; directing a second portion of the stream of separated components out of the switching region and into a collection leg of the device; directing a third portion of the stream of separated components out of the switching region and into the waste leg of the device; and collecting a separated component from a collection well disposed in the collection leg.

The aforementioned and other features and advantages of the invention will become further apparent from the following detailed description of the presently preferred embodiments, read in conjunction with the accompanying drawings, which are not to scale. In the drawings, like reference numbers indicate identical or functionally similar elements. The detailed description and drawings are merely illustrative of the invention, rather than limiting, the scope of the invention being defined by the appended claims and equivalents thereof.

DETAILED DESCRIPTION OF THE PRESENTLY PREFERRED EMBODIMENTS

Figure 1:
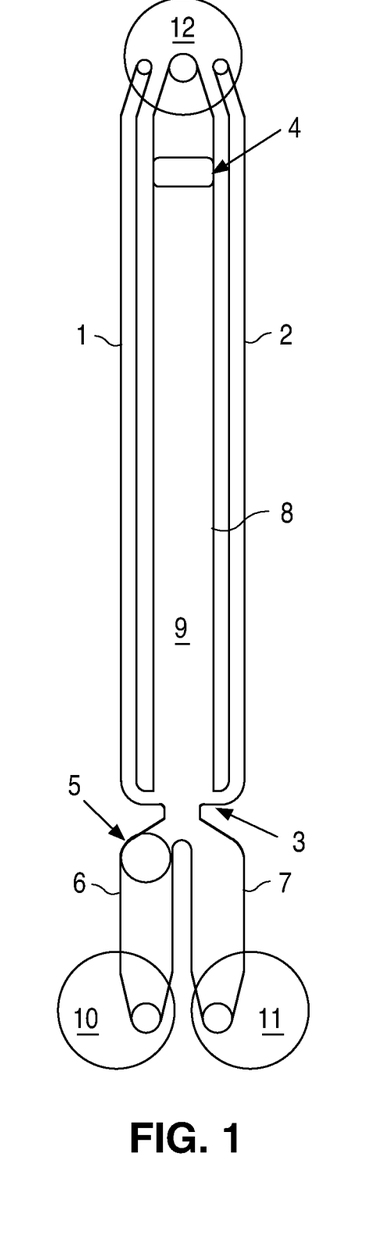
FIG. 1 is a schematic illustration of a device for isolating one or more sample components of a sample material following separation of the sample material into a plurality of sample components, in accordance with the present invention.

One aspect of the present invention is a device for isolating one or more sample components of a sample material following separation of the sample material into a plurality of sample components. One embodiment of the device, in accordance with the present invention, is illustrated in FIG. 1. The illustrated device comprises first and second pinching channels 1 and 2, a switching region 3, a loading well 4, a collection well 5, a collection leg 6, a waste leg 7, a separation channel 8, a sieving matrix 9, and reservoirs 10-12. In the present embodiment, reservoirs 10 and 11 are waste reservoirs, while reservoir 12 is a buffer reservoir.

As seen in FIG. 1, pinching channels 1 and 2 extend from reservoir 12 to switching region 3. Separation channel 8 also extends from reservoir 12 to switching region 3 and is positioned between pinching channels 1 and 2. The three channels merge at the inlet end of switching region 3. By having pinching channels 1 and 2 join separation channel 8 just above the switching region, little diffusion of the sample into the buffer streams occurs. Separation channel 8 includes a loading well 4 that is open to the external environment to permit a sample to be deposited into the loading well manually using, for example, a pipettor, or a sample may be deposited by an automated sample transfer device.

Figure 2:
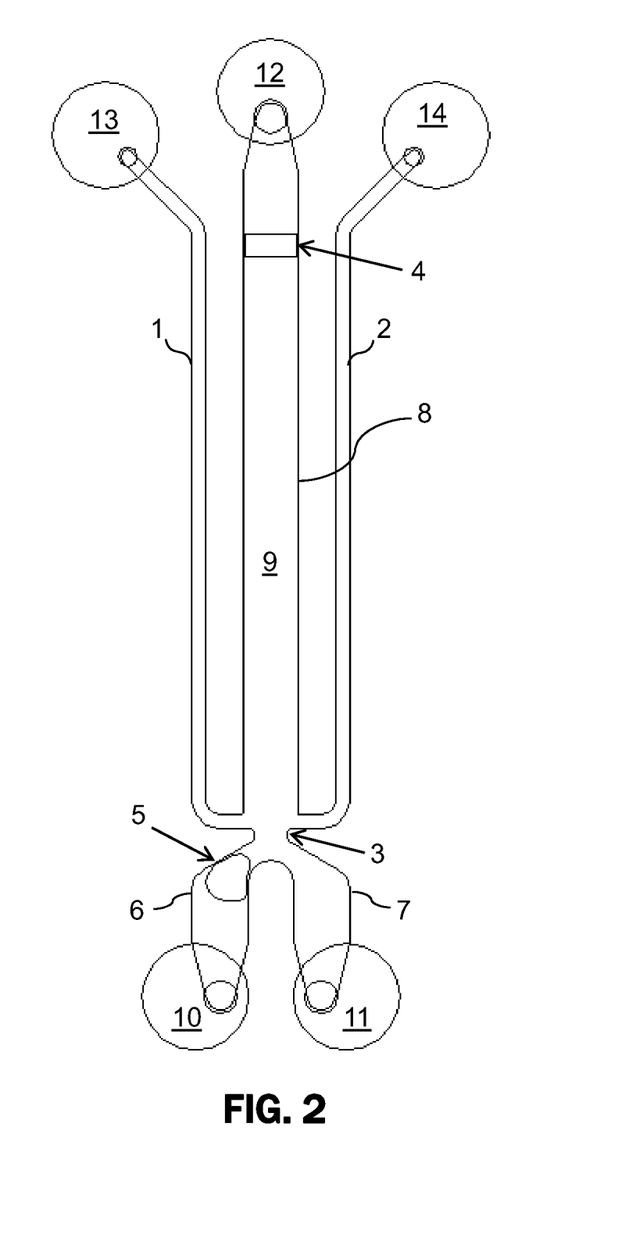
FIG. 2 is a schematic illustration of another device for isolating one or more sample components of a sample material following separation of the sample material into a plurality of sample components, in accordance with the present invention.

Legs 6 and 7 extend from the outlet end of switching region 3 to reservoirs 10 and 11, respectively. As seen in FIG. 1, collection well 5 is positioned in collection leg 6. The collection well may be positioned anywhere in the collection leg between switching region 3 and reservoir 10. Positioning the collection well nearer to the switching region than to the reservoir may permit collection of a narrower, i.e., more precisely selected, band of the separated sample material. A larger collection well may permit collection of a broader band. Collection well 5 is open to the external environment to permit removal of the isolated sample component(s) from the device. Collection well 5 may be circular as seen in FIG. 1 or may be any other shape that facilitates collecting the isolated sample component(s). For example, a free-form shape is shown in FIG. 2. While the collection well is shown in leg 6 in the illustrations, it may alternatively be positioned in leg 7 in another embodiment. In this alternative embodiment, leg 6 would then be the waste leg, and leg 7 would be the collection leg.

Separation channel 8 may include a sieving matrix 9 to facilitate electrophoretic separation of a sample within the separation channel. The sieving matrix may be, for example, agarose or a cross-linked gel. Pinching channels 1 and 2, switching region 3, legs 6 and 7, and reservoirs 10-12 may also include the sieving matrix, although reservoirs 10-12 are not completely filled with the sieving matrix and additionally contain a buffer. Loading well 4 and collection well 5 do not include the sieving matrix in order to facilitate introduction and withdrawal of sample materials. In alternative embodiments, the device may include a sieving matrix in only some or none of pinching channels 1 and 2, switching region 3, legs 6 and 7, separation channel 8 and reservoirs 10-12.

Switching region 3 may be a simple intersection of the channels entering and exiting the region, or the switching region may be extended to form a channel. Switching region 3 is shown as a narrowed "neck" in FIGS. 1 and 2 (i.e., the cross-sectional dimension [width] of the separation channel is shown as being greater than the cross-sectional dimension [width] of the switching region). Other geometries are possible. The narrowed switching region is desirable because it both increases the electric field and therefore the migration velocity within the region and helps to prevent bubbles being trapped in a separation matrix during filling of the device. However, as will be discussed further below, the switching region need not be substantially narrowed for the electric field to be increased within the separated sample in the switching region because the sample stream is "pinched," i.e., constrained or contained and thereby elongated, by buffer transported into the switching region from the two pinching channels, increasing the current density (and therefore the electric field) and creating a faster electrophoretic velocity in the sample material within the switching region. Pinching of the sample stream can be seen in FIG. 3, where the sample stream appears light and buffer streams appear dark at the switching region.

Figure 4:
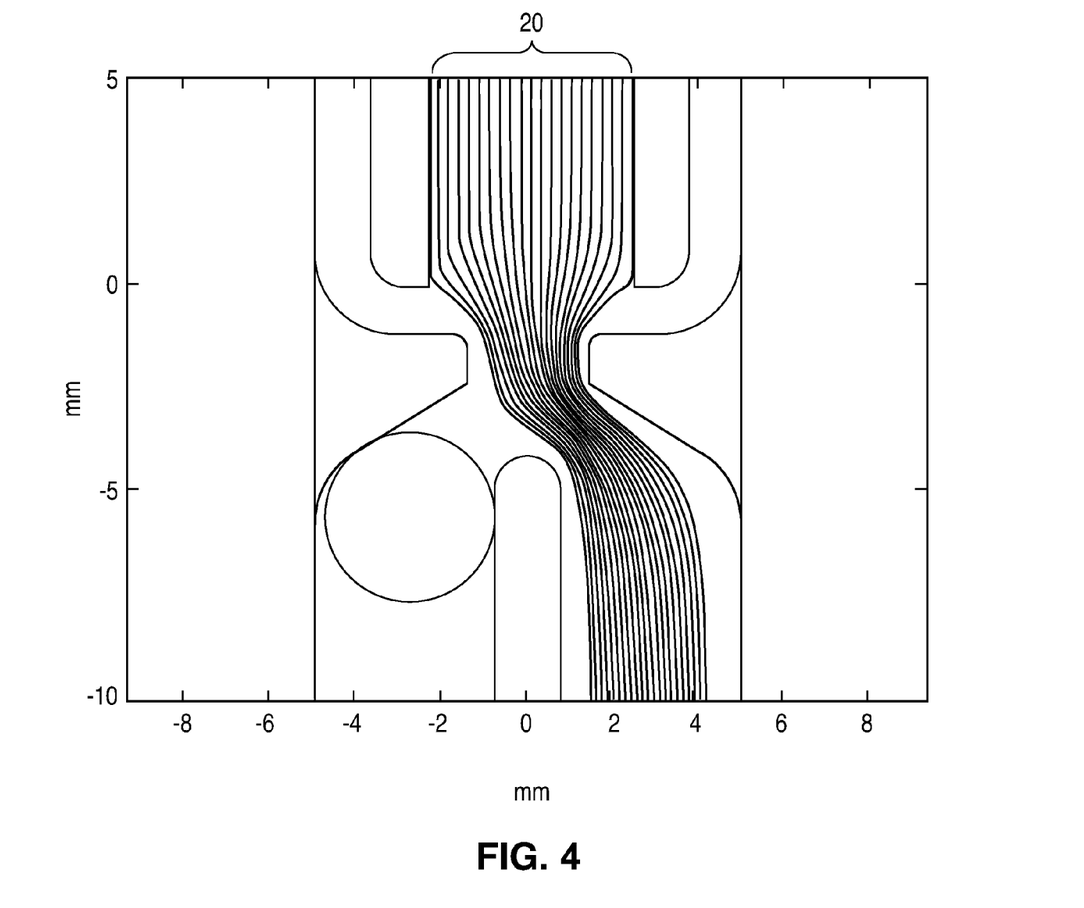
FIG. 4 is a schematic illustration of a portion of the device of FIG. 1 showing stream lines achieved using the pinching channels of the device.
Figure 5:
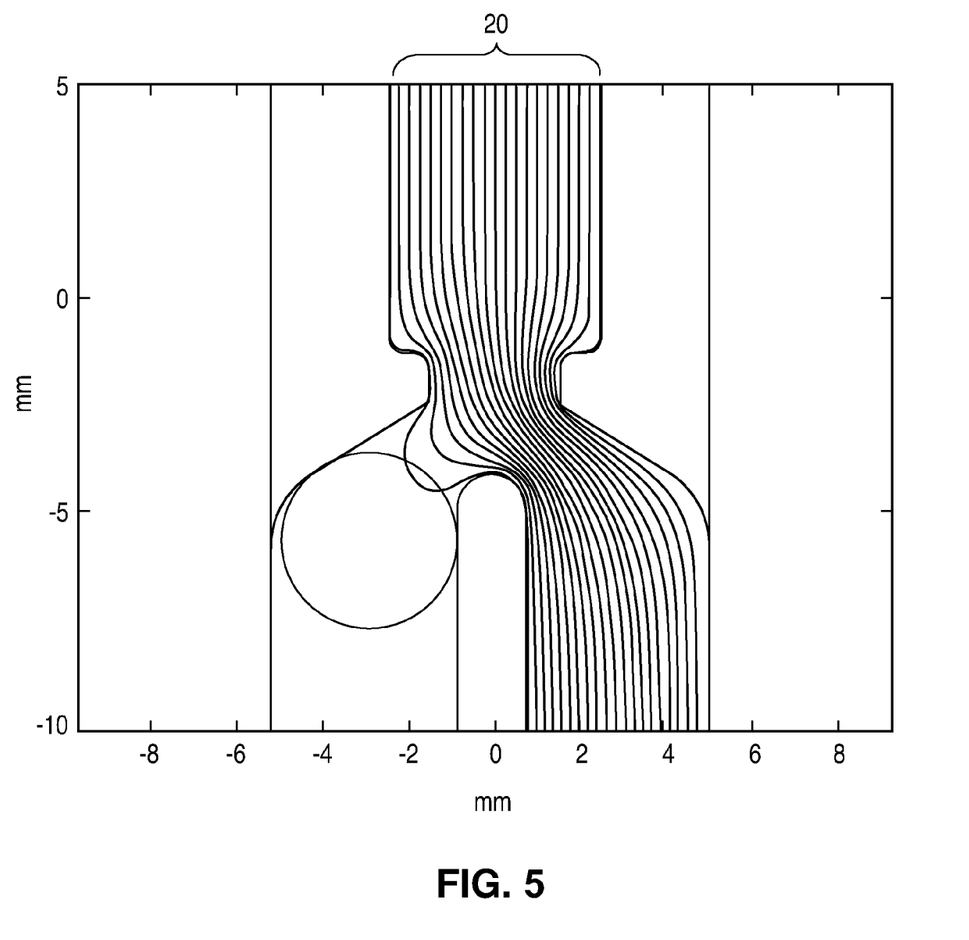
FIG. 5 is a schematic illustration of a portion of a device without pinching channels showing stream lines achieved without the benefit of the pinching channels of the device of FIG. 1.

Pinching of the sample can also be seen in FIG. 4, which models transport of sample materials through a portion of the device of FIG. 1. As can be seen by the stream lines illustrated at 20 in FIG. 4, the entire sample stream is directed away from collection leg 6 and collection well 5. Contrast FIG. 4 with FIG. 5, which models transport of sample materials through a portion of a device that does not include pinching channels. Stream lines 20 of FIG. 5 show that a portion of the sample stream strays into the collection leg and collection well of the device of FIG. 5, resulting in unwanted sample components being present in the collection well when pinching streams are not employed.

Another embodiment of the device, in accordance with the present invention, is illustrated in FIG. 2. Note that throughout the figures, like elements share like reference numbers. The illustrated device comprises first and second pinching channels 1 and 2, a switching region 3, a loading well 4, a collection well 5, a collection leg 6, a waste leg 7, a separation channel 8, a sieving matrix 9, and reservoirs 10-14. In the embodiment illustrated in FIG. 2, reservoirs 10 and 11 are waste reservoirs, while reservoirs 12-14 are buffer reservoirs. Refer to the discussion above for descriptions of elements 1-12. The embodiment shown in FIG. 2 differs from the embodiment shown in FIGS. 1 and 4 in that the device of FIG. 2 includes three buffer reservoirs rather than a single buffer reservoir.

In the embodiment of FIG. 1, pinching channels 1 and 2 share the same reservoir (reservoir 12) with separation channel 8. In this embodiment, the pinching ratio (the ratio of the electrical current in the separation channel to the current in the pinching channels) is controlled by the ratio of the pinching channel resistance to the separation channel resistance, resistance being a function of the geometry (e.g., width, depth, length) of the channel. Having a shared reservoir for the separation channel and the two pinching channels offers the benefit of minimizing the number of electrodes and power supplies required by the device, resulting in a highly compact device.

In the embodiment of FIG. 2, each of channels 1, 2, and 8 has its own separate reservoir, reservoirs 13, 12, and 14, respectively. By having separate reservoirs for each of the pinching channels and the separation channel, the pinching ratio can be controlled independent of the geometry of the channels. This may be accomplished by, for example, applying different voltages at the different reservoirs or controlling the current ratio between the separation channel and pinching channels directly using external hardware such as a power supply. Note that increasing the pinching ratio will provide better containment of the sample within the switching region at the cost of more current/power needed.

Either of the embodiments described above may include a detection region (not shown) within which the sample component(s) intended for collection are detected in order to switch the desired component(s) into the collection leg. Alternatively, the sample component(s) may be identified based on a known transit time through the device.

The materials of the device are chosen for their suitability for electrophoretic separations and for their inertness to the components to be separated and isolated in the device. Materials suitable for the device include, but are not limited to, glass and other ceramics, quartz, silicon, and polymeric substrates, e.g., plastics.

Another aspect of the present invention is a system for isolating one or more sample components of a sample material following separation of the sample material into a plurality of sample components. The system comprises a device such as has been described above as well as instrumentation for controlling the device. For example, the system may comprise a detector 15 positioned in sensory communication with a detection region of the device, a processor 16 operably coupled to the detector and to a fluid direction system 17 that is configured to control movement of one or more sample components from the separation channel into the collection well of the collection leg based on information received from the detector. As used herein, the phrase "in sensory communication" refers to positioning of a detector such that it is operably connected to the device, i.e., capable of receiving a detectable signal from the contents of the device. In the case of optical signals, this requires only that the detector be positioned to receive the optical signal. In a preferred aspect of the invention, the processor comprises a computer that includes appropriate programming for receiving a signal from the detector that is indicative of a separated component passing the detector, determining a retention time of the separated components in the separation channel, and determining a size of the separated components by comparing the retention time of the separated components to a retention time of components of a standard reference of known size for the sample material. The system may be configured to simultaneously control multiple fluidic circuits (a single fluidic circuit being shown, e.g., in FIG. 1). In such a configuration, the fluid direction system may be configured to control the movement of one or more sample components in one fluidic circuit based on information received by the detector in a parallel circuit.

Yet another aspect of the present invention is a method for isolating one or more sample components of a sample material following separation of the sample material into a plurality of sample components. The method may be carried out using a device or system such as has been described above and illustrated in FIGS. 1 and 2. The description below refers to the illustrated embodiments of the device, but the method may be varied depending on the geometry of the device used, various changes and modifications to the device being both possible and foreseen.

One or more buffers are loaded into the buffer reservoir(s). In an alternative embodiment of the method, the device may be supplied with buffer already loaded into the reservoir(s). A low-ionic strength buffer may be loaded into collection well 5 and a higher ionic strength buffer may be loaded into all other reservoirs and channels. A low ionic strength buffer may be preferred for the collection well if the isolated sample component(s) will later undergo amplification using PCR. A higher ionic strength buffer may be preferred for the reservoirs to provide additional buffering capacity. Current may be passing through these channels for extended periods, for example up to 60 minutes, and a higher buffer concentration may mitigate changes in pH within the device due to the passage of current through the device. In addition, field amplified sample stacking (FASS) will occur when a higher conductivity buffer is used in the separation channel and the input sample is loaded in a low conductivity buffer. FASS will increase the sensitivity and resolution of the separation.

A sample is deposited into the loading well, shown at 4 in FIGS. 1 and 2. The sample may be deposited manually using, for example, a pipettor, or may be deposited by an automated sample transfer device. A voltage is applied to buffer reservoir 12, and a different voltage is applied to waste reservoir 11 to electrophoretically separate the sample into a plurality of sample components in separation channel 8. Initially, no electrical connection is made to waste reservoir 10 in order to maintain zero current within collection leg 6, thereby directing the separated sample into waste leg 7 and waste reservoir 11 until a component of the sample desired for isolation and collection reaches switching region 3. Alternatively, the fluid direction system may control the voltage at waste reservoir 10 in order to maintain zero current. Note that the term "zero current" is defined herein as a current that is negligible as compared to the current in the other leg, such as a current that is less than 2% of the current in the other leg.

Figure 3:
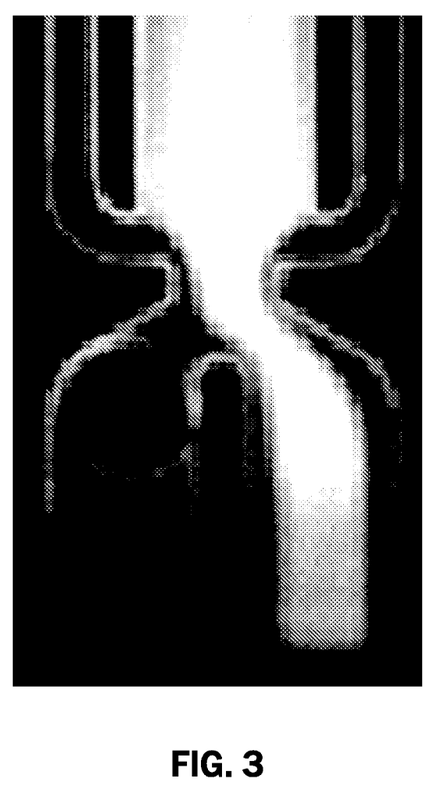
FIG. 3 is a photograph of a portion of a device in accordance with the present invention, the device shown during operation.

At the same time that the sample is being separated in separation channel 8, buffer is being transported through pinching channels 1 and 2 as a result of a voltage difference between waste reservoir 11 and the buffer reservoir connected to each of the pinching channels (reservoir 12 in FIG. 1, and reservoirs 13 and 14 in FIG. 2). As the separated sample passes through switching region 3, the buffer streams from the two pinching channels "pinch" (i.e., constrain or contain) the separated sample as seen in FIGS. 3 and 4, thereby increasing the field and creating a faster electrophoretic velocity in the sample material within the switching region. Pinching of the sample prevents leakage of the sample into the non-target leg. Leakage can be seen in FIG. 5, which illustrates a device that does not include pinching channels. Initially, the non-target leg is collection leg 6. Waste leg 7 remains the target leg until the component(s) to be isolated enter switching region 3, and the sample stream is momentarily switched, i.e., diverted, into collection leg 6, which then becomes the target leg.

Once the one or more components that are to be isolated and collected are within switching region 3, a voltage is applied to waste reservoir 10, and a zero current is maintained at waste reservoir 11. This switches the direction of the sample stream from waste leg 7 into collection leg 6. The redirection of the sample stream is timed to isolate only the desired component(s) of the sample. Once the one or more desired components are within collection leg 6 and positioned at the location of collection well 5, the sample stream is directed back into waste leg 7 and waste reservoir 11 by once again controlling zero current to waste reservoir 10 and resuming the original voltage to waste reservoir 11. Once zero current is imposed at the electrical connection to waste reservoir 10, transport into collection leg 6 stops, and the desired one or more components of the sample remain in place within collection leg 6 at the location of collection well 5. The sample component(s) may then be removed from collection well 5 manually using, for example, a pipettor, or may be withdrawn by an automated sample transfer device.

As described above, the pinching ratio of the device illustrated in FIG. 1 is controlled by the ratio of the pinching channel resistance to the separation channel resistance, resistance being a function of the geometry of the channel. The pinching ratio of the device illustrated in FIG. 2 can be controlled independently of the geometry, for example by applying different voltages at the various reservoirs or controlling the current ratio between the separation channel and pinching channels directly using external hardware such as a power supply. Increasing the pinching ratio provides better confinement of the sample at the switching region at the cost of needing more current/power.

As has been discussed previously, pinching the sample stream as it is transported into switching region 3 increases the field and creates a faster electrophoretic velocity in the sample material within the switching region as compared to that within the separation channel. The value of pinching can be readily understood when placed in context. When fractionating DNA, for example, the higher velocity decreases the number of base pairs per unit distance. That is, as the ratio of the velocity in the switching region to the velocity in the separation channel is increased, the number of base pairs within switching region 3 is decreased, in effect "stretching out" the separated sample and elongating the sample stream. This increases the precision of diverting a small band comprising the desired component(s) to collection leg 6 because the physical size of the switching intersection is in some ways equivalent to the thickness of a scalpel blade used to cut a slice containing one or more bands out of a gel. When cutting a gel, the thickness of the blade determines the minimum size slice that can be cut from the gel because it is difficult (practically impossible) to cut a slice that is thinner than the thickness of the blade. If the gel could be stretched, a more precise selection could be cut from the gel using the same size scalpel. By the same token, in the present method, increasing the pinching ratio will increase the resolution of the "cut" performed by the device. Other methods besides or in addition to increasing the pinching ratio may be used to increase the velocity at the switching region. Any method that increases either the electric field or species mobility will be effective. Such methods include (but are not limited to) the following: changing the depth of the channel at the switching region, changing or removing the sieving matrix near the switching region (so as to increase the mobility of species) or creating a step reduction in conductivity near the region.

While the sample is being separated, it is desirable to maintain the same separation field within the separation channel regardless of whether sample is being sent to the left (collection leg 6) or the right (waste leg 7). The collection well (seen at 5 in FIGS. 1 and 2) may, for example, contain buffer of a different conductivity than the running buffer, i.e., the buffer being transported through separation channel 8. As mentioned above, buffers of different conductivity may be used within the device, with a higher conductivity buffer in one or more of the channels than is present in collection well 5. Thus, the resistance could be different in the two legs and the exact value of the resistance unknown. Such uncertainty in the channel resistances means that the fluid direction system cannot maintain the same electric field in separation channel 8 when the target leg is switched. To overcome this problem, voltage may be controlled at the switching region by reading the voltage at the leg that has zero current. See FIG. 6. That is, because zero current is maintained in one leg, e.g., in leg 6, the voltage in leg 6 is the same throughout the leg, all the way up to switching region 3; therefore, reading the voltage in leg 6 becomes a way of measuring the voltage in the switching region ($V_i$). By adjusting the voltage and/or current in the other leg, leg 7, a desired $V_i$ may be maintained at the switching region.

Figure 6:
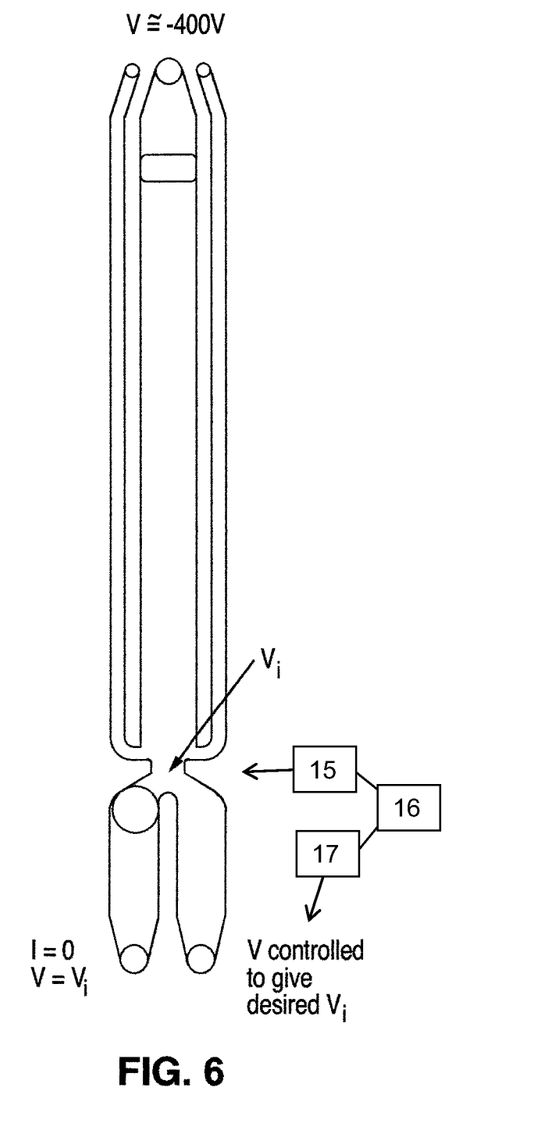
FIG. 6 is a schematic illustration of a system comprising the device of FIG. 1 and including information regarding a feedback control mechanism.

In this way, the voltage drop between the sample loading well (seen at 5 in FIGS. 1 and 2) and the switching region (seen at 3 in FIGS. 1 and 2) will remain substantially the same, even if the resistances of the two legs are unknown (and possibly unequal). This feedback control is enabled by the design of the device because the pinching channels allow for confinement of the sample at the switching region even when there is zero current on one of the legs, as illustrated in FIG. 6.

Feedback control is achieved using an electrical circuit that controls and applies voltages and currents to electrodes connected to reservoirs of the device. The electrical circuit may include semiconductor and/or electromechanical devices used as switches. The switches may be used in linear (proportional) and/or non linear (ON/OFF) modes of operation. The electrical circuit may be computer controlled so that the magnitude of the applied voltages and currents, and the timing of their application, are specified by a computer algorithm, which may also be driven by the signal from the detector. The computer system may additionally be used to display, process, analyze, and store information gathered as a result of the operation of the device.

Using the device, fragments of a specific size may be isolated from an initial sample having a wide size distribution. For many applications, the goal is to isolate a band of narrow size distribution in the collection well. However, for other applications, a wider size distribution may be desired or tolerated in exchange for collection of more mass. As can be seen in FIG. 1, collection well 5 is not necessarily the terminus of the electrical circuit. Therefore, material entering collection well 5 will continue to electrophorese towards reservoir 10, eventually passing out of the collection well. In this way, the size of collection well 5 influences the maximum amount of material that can be collected since the smallest, fastest moving fragments will eventually leave the collection well as larger, slower fragments continue to enter.

The amount of material that can be collected may be increased by increasing the size of the collection well, by making this well the terminus of the electrical circuit, or by using a higher conductivity (or higher viscosity, or increased sieving) buffer in collection well 5. This will be possible if the sieving matrices in the channels are cross-linked or gelled. In this case, the collection well will be defined as a "hole" in the matrix that can be filled with a different buffer. When the collection buffer (the buffer in the collection well) is a higher conductivity than the running buffer (the buffer in the collection leg), material entering the well will concentrate and slow down (i.e., become stacked). Thus, for example, if the collection buffer is twice the conductivity of the running buffer, then the capacity of the collection well will be doubled. Alternatively, other methods of stacking may be used, such as increasing the viscosity, increasing the sieving or decreasing the current density (by increasing the cross-sectional area at the collection well). The viscosity may be increased by adding agents such as glycerol to the collection buffer. The sieving may be increased by adding polymers (such as PDMA) that impede the progress of the separated molecules.

Figure 7:
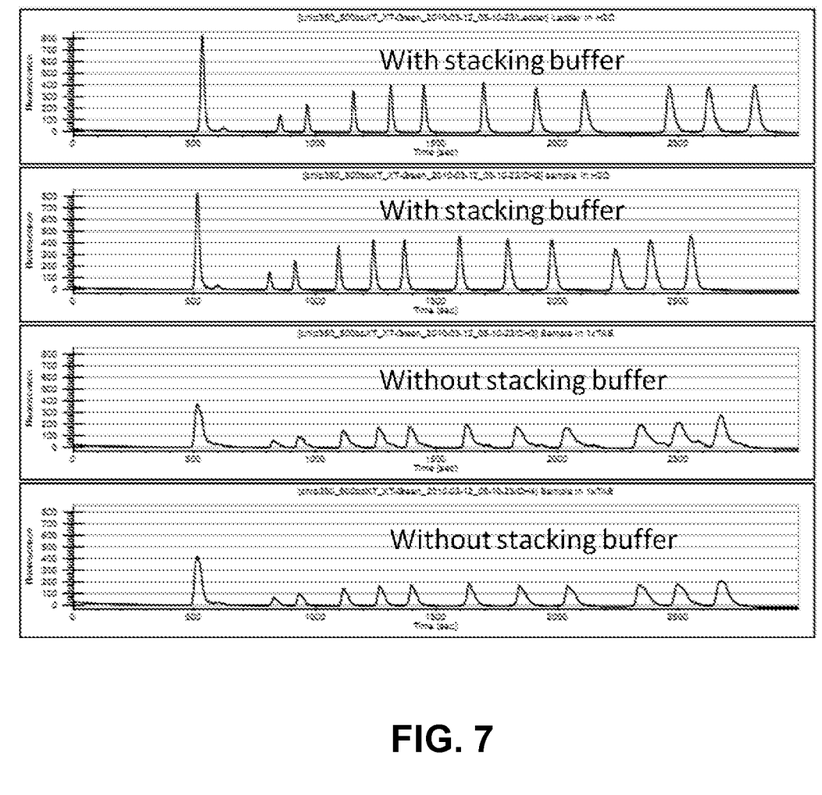
FIG. 7 is an illustration of the effect on DNA separation resolution of a low-conductivity buffer disposed over a sample material in a sample loading well.
Figure 8:
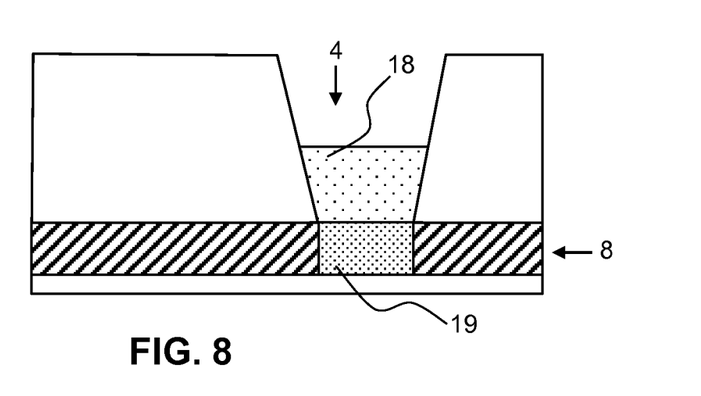
FIG. 8 is a schematic illustration of a loading well having both a sample solution and a low-conductivity buffer disposed in the well.
Figure 10:
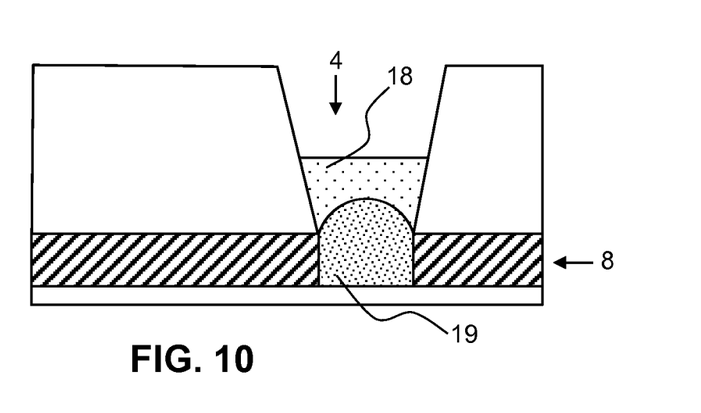
FIG. 10 is a schematic illustration of a loading well having both a sample solution and a low-conductivity buffer disposed in the well, the sample solution having been filled above the height of the channel.

Stacking may be improved by depositing a low-conductivity buffer in a sample loading well prior to loading a sample material into the well. The sample material is then loaded in such a way that the sample material is deposited at the bottom of the well with the low-conductivity buffer disposed over and covering the sample material as seen in FIGS. 8 and 10. The buffer (seen at 18) has a conductivity lower than that of the sample material (seen at 19) that is to be disposed in the loading well. Preferably, the buffer has a conductivity<0.2 mS/cm. Because the conductivity of the buffer is lower than that of the sample material disposed beneath the buffer, the buffer substantially confines the electric field lines to remain within the sample material, minimizing dispersion of the sample material and resulting in more clearly defined sample component peaks as illustrated in FIG. 7. The buffer is identified as a "stacking" buffer in FIG. 7.

The buffer may comprise, for example, deionized water. Neutral polymers such as poly(dodecyl methacrylate) (PDMA), hydroxyethyl cellulose (HEC), hydroxypropyl methylcellulose (HPMC), and combinations thereof may be added to the deionized water to aid in suppressing electroosmotic flow in the loading well. The buffer may also comprise low dielectric liquids immiscible with an aqueous solution. Such low dielectric liquids include, for example, low molecular weight alkane hydrocarbons such as decane and dodecane.

To ensure the sample material remains disposed at the bottom of the loading well, the sample material may be ≥5% glycerol by weight to cause the sample material to be heavier than the buffer.

Figure 9:
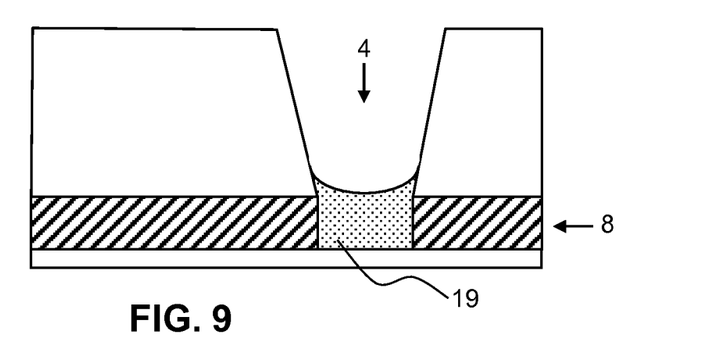
FIG. 9 is a schematic illustration of a loading well having only a sample solution disposed in the well.

Use of the low-conductivity buffer in a loading well improves injection not only by way of electric-field confinement, but also by eliminating any meniscus at the top edge of the sample material. As can be seen in FIG. 8, depositing the sample material beneath the low-conductivity buffer eliminates a gas-liquid interface between the sample material and air disposed within or above the loading well. FIG. 9 illustrates a loading well that contains a sample material with no buffer disposed over the sample material. As can be seen, a gas-liquid interface within the loading well results in wicking of the sample material up onto the walls of the well. Such wicking causes a meniscus of sample that may be poorly loaded into the channel because the electric field in the corners of the meniscus is very low.

Note that it is possible to load sample material above the height of the channel into which the sample material is injected (as seen in FIG. 10) provided that the interface between the low-conductivity buffer and the sample material remains sufficiently well defined. This is possible because the interface between the low conductivity buffer and the higher conductivity sample material acts as a virtual wall that contains the electric field and allows for clean injection of all of the sample.

Thus, one embodiment of a device for isolating one or more sample components of a sample material following separation of the sample material into a plurality of sample components, in accordance with the present invention, includes a separation channel 8 having first and second ends. A loading well 4 is disposed in the separation channel, and a quantity of a buffer 18 is disposed in the loading well. The buffer has a conductivity<0.2 mS/cm and may comprise materials as described above. The device includes a collection leg 6 having first and second ends, the collection leg having a collection well 5 disposed between the first and second ends, a waste leg 7 having first and second ends, and a switching region 3 having an inlet end and an outlet end. The second end of separation channel 8 is in fluid communication with the inlet end of switching region 3, and the first end of collection leg 6 and the first end of waste leg 7 are in fluid communication with the outlet end of switching region 3. Separation channel 8 may have a sieving matrix 9 disposed therein. The separation channel in FIGS. 8-10 is shown including a sieving matrix.

The device may include a first buffer reservoir 12, a first waste reservoir 10, and a second waste reservoir 11. The first end of separation channel 8 is in fluid communication with buffer reservoir 12, the second end of collection leg 6 is in fluid communication with first waste reservoir 10, and the second end of waste leg 7 is in fluid communication with second waste reservoir 11.

The device may also include first and second pinching channels 1 and 2, each pinching channel having a first end and a second end. The second end of each of the first and second pinching channels is in fluid communication with the inlet end of switching region 3. The first ends of the first and second pinching channels may be in fluid communication with buffer reservoir 12. Alternatively, the device may further include a second buffer reservoir 13 and a third buffer reservoir 14, with the first end of first pinching channel 1 in fluid communication with second buffer reservoir 13, and the first end of second pinching channel 2 in fluid communication with third buffer reservoir 14. The device may further comprise a quantity of a sample material 19 disposed in the loading well beneath buffer 18. The sample material may be ≥5% glycerol by weight.

A method for isolating one or more sample components of a sample material following separation of the sample material into a plurality of sample components, in accordance with the present invention, comprises loading a buffer into a loading well in fluid communication with a separation channel of a device. The device may be one such as has been described above. The buffer has a first conductivity. The first conductivity may be <0.2 mS/cm. A sample material is loaded into the loading well such that the sample material is disposed beneath the buffer, the buffer disposed over and covering the sample material. The sample material has a second conductivity, the second conductivity of the sample material being higher than the first conductivity of the buffer. The sample material may be loaded by inserting a pipette tip into the loading well such that it is immersed in the buffer and dispensing the sample material through the pipette tip into the loading well. The sample material is preferably dispensed slowly to avoid mixing with the buffer.

The sample material is separated into a plurality of separated components in the separation channel, the separated components forming a stream. The stream of separated components is transported into a switching region of the device. A first portion of the stream of separated components is directed out of the switching region and into a waste leg of the device. A second portion of the stream of separated components is directed out of the switching region and into a collection leg of the device. A third portion of the stream of separated components is directed out of the switching region and into the waste leg of the device. A separated component is collected from a collection well disposed in the collection leg.

The method may further comprise transporting first and second buffer streams into the switching region on either side of the component stream such that the first and second buffer streams constrain and elongate the component stream as it is transported through the switching region. In this embodiment, a first portion of the first buffer stream and a first portion of the second buffer stream are directed out of the switching region and into the waste leg of the device. A second portion of the first buffer stream and a second portion of the second buffer stream are directed out of the switching region and into the collection leg of the device. A third portion of the first buffer stream and a third portion of the second buffer stream are directed out of the switching region and into the waste leg of the device.

While the embodiments of the invention disclosed herein are presently considered to be preferred, various changes and modifications can be made without departing from the spirit and scope of the invention. The scope of the invention is indicated in the appended claims, and all changes and modifications that come within the meaning and range of equivalents are intended to be embraced therein.

What is claimed is:

1. A device for isolating one or more sample components of a sample material following separation of the sample material into a plurality of sample components, comprising:
    a separation channel having a first end and a second end, the separation channel having a separation channel axis along a straight length of the separation channel at the second end;
    a loading well disposed in the separation channel;
    a collection leg having a first end and a second end;
    a collection well disposed in the collection leg between the first and second ends of the collection leg;
    a waste leg having a first end and a second end; and
    a switching region having an inlet end and an outlet end;
    a first pinching channel having a first end and a second end, the first pinching channel having a first pinching channel connection portion, the first pinching channel connection portion having a first pinching channel axis along a straight length of the first pinching channel connection portion at the second end of the first pinching channel;
    a second pinching channel having a first end and a second end, the second pinching channel having a second pinching channel connection portion, the second pinching channel connection portion having a second pinching channel axis along a straight length of the second pinching channel connection portion at the second end of the second pinching channel;
    wherein the second end of each of the first pinching channel, the second pinching channel, and the separation channel are in fluid communication with the inlet end of the switching region;
    the separation channel axis is perpendicular to the first pinching channel axis, the separation channel axis is perpendicular to the second pinching channel axis, and the first pinching channel axis and the second pinching channel axis are collinear; and
    the first end of the collection leg and the first end of the waste leg are in fluid communication with the outlet end of the switching region.

2. The device of claim 1 wherein the buffer comprises deionized water.

3. The device of claim 2 wherein the buffer further comprises an additive selected from a group consisting of PDMA, HEC, HPMC, another neutral polymer, and combinations thereof.

4. The device of claim 1 wherein the buffer comprises a low dielectric liquid immiscible with an aqueous solution.

5. The device of claim 1 further comprising a first buffer reservoir, a first waste reservoir, and a second waste reservoir, wherein the first end of the separation channel is in fluid communication with the first buffer reservoir, the second end of the collection leg is in fluid communication with the first waste reservoir, and the second end of the waste leg is in fluid communication with the second waste reservoir.

6. The device of claim 1 wherein the first ends of the first and second pinching channels are in fluid communication with the first buffer reservoir.

7. The device of claim 1 further comprising a second buffer reservoir and a third buffer reservoir, wherein the first end of the first pinching channel is in fluid communication with the second buffer reservoir and the first end of the second pinching channel is in fluid communication with the third buffer reservoir.

8. The device of claim 1 further comprising a quantity of a sample material disposed in the loading well beneath the buffer.

9. The device of claim 8 wherein the sample material is >5% glycerol by weight.

10. The device of claim 8 wherein the sample material is disposed in the loading well such that the sample material extends above a height of the separation channel.

11. A method of separating a sample material into a plurality of separated components and isolating one or more of the separated components in a device, the method comprising:
   loading a buffer into a loading well in fluid communication with a separation channel of a device, the buffer having a first conductivity,
   loading a sample material into the loading well such that the sample material is disposed beneath the buffer, the buffer disposed over and covering the sample material, the sample material having a second conductivity, the second conductivity being higher than the first conductivity;
   separating the sample material into a plurality of separated components in the separation channel, the separated components forming a stream;
   transporting the stream of separated components into a switching region of the device;
   transporting first and second buffer streams into the switching region on either side of the stream of separated components such that the first and second buffer streams constrain and elongate the stream of separated components as the stream of separated components is transported through the switching region;
   directing a first portion of the first buffer stream and a first portion of the second buffer stream out of the switching region and into the waste leg of the device;
   directing a second portion of the first buffer stream and a second portion of the second buffer stream out of the switching region and into the collection leg of the device;
   directing a third portion of the first buffer stream and a third portion of the second buffer stream out of the switching region and into the waste leg of the device;
   directing a first portion of the stream of separated components out of the switching region and into a waste leg of the device;
   directing a second portion of the stream of separated components out of the switching region and into a collection leg of the device;
   directing a third portion of the stream of separated components out of the switching region and into the waste leg of the device; and
   collecting a separated component from a collection well disposed in the collection leg.

12. The method of claim 11 wherein loading a sample material into the loading well comprises inserting a pipette tip into the loading well such that it is immersed in the buffer and dispensing the sample material through the pipette tip into the loading well beneath the buffer.

13. The method of claim 11 wherein the first conductivity is <0.2 mS/cm.

14. The method of claim 11 wherein the buffer comprises deionized water.

15. The method of claim 11 wherein the buffer further comprises an additive selected from a group consisting of PDMA, HEC, HPMC, another neutral polymer, and combinations thereof.

16. The method of claim 11 wherein the buffer comprises a low dielectric liquid immiscible with an aqueous solution.

17. The method of claim 11 wherein the sample material is >5% glycerol by weight.

18. The device of claim 11 wherein loading a sample material into the loading well further comprises loading the sample material such that the sample material extends above a height of the separation channel.

19. A device for isolating one or more sample components of a sample material following separation of the sample material into a plurality of sample components, the device comprising:
   first and second pinching channels, each of the pinching channels having a first end and a second end, each of the pinching channels having a connection portion at the second ends, each of the connection portions having a pinching channel axis along a straight length of the connection portion at the second end;
   a separation channel positioned between the first and second pinching channels, the separation channel having a first end and a second end, the separation channel having a separation channel axis along a straight length of the separation channel at the second end;
   a switching region having an inlet end and an outlet end, the cross-sectional dimension of the switching region being less than the cross-sectional dimension of the separation channel;
   wherein the second ends of each of the first pinching channel, the second pinching channel, and the separation channel are in fluid communication with the inlet end of the switching region;
   the separation channel axis is perpendicular to each of the first pinching channel axis and the second pinching channel axis; and
   the pinching channel axis of the first pinching channel is collinear with the pinching channel axis of the second pinching channel.

20. The device of claim 19, wherein the switching region is the intersection of the first and second pinching channels and the separation channel.

21. The device of claim 19, wherein the switching region is a channel.

22. The device of claim 19, wherein the switching region is a narrowed neck.

23. The device of claim 19, further comprising a first stream entering the switching region from the first pinching channel, a second stream entering the switching region from the second pinching channel, and a sample stream entering the switching region from the separation channel, the first stream and the second stream surrounding the sample stream, wherein a cross-sectional dimension of the switching region is selected to constrain and elongate the sample stream as the sample stream, the first stream, and the second stream pass through the switching region.

24. The device of claim 23 wherein the first stream is a first buffer stream and the second stream is a second buffer stream.

* * * * *